(12) United States Patent
Sherman et al.

(10) Patent No.: US 9,476,637 B2
(45) Date of Patent: Oct. 25, 2016

(54) ILLUMINATION DEVICE HAVING REMOTELY POWERED LIGHTGUIDE

(71) Applicant: 3M INNOVATIVE PROPERTIES COMPANY, St. Paul, MN (US)

(72) Inventors: Audrey A. Sherman, Woodbury, MN (US); Kevin R. Schaffer, Woodbury, MN (US); Michael A. Meis, Stillwater, MN (US); Soemantri Widagdo, Depok (ID)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 194 days.

(21) Appl. No.: 14/518,402

(22) Filed: Oct. 20, 2014

(65) Prior Publication Data

US 2015/0062961 A1   Mar. 5, 2015

Related U.S. Application Data

(63) Continuation of application No. 13/501,335, filed as application No. PCT/US2010/054761 on Oct. 29, 2010, now Pat. No. 8,864,362.

(60) Provisional application No. 61/263,495, filed on Nov. 23, 2009, provisional application No. 61/256,827, filed on Oct. 30, 2009.

(51) Int. Cl.
*F25D 27/00* (2006.01)
*F21V 7/00* (2006.01)
(Continued)

(52) U.S. Cl.
CPC ............. *F25D 27/00* (2013.01); *F21V 7/0091* (2013.01); *G02B 6/0083* (2013.01); *G04G 19/00* (2013.01); *A44C 5/14* (2013.01); *A44C 15/0015* (2013.01); *A61N 2005/0645* (2013.01); *F21S 9/03* (2013.01); *F21V 23/00* (2013.01); *G02B 6/0065* (2013.01); *G02B 6/0081* (2013.01); *G02B 6/0095* (2013.01); *H02J 17/00* (2013.01)

(58) Field of Classification Search
CPC ... F25D 27/00; F21V 7/0091; G02B 6/0083; G04G 19/00
See application file for complete search history.

(56) References Cited

U.S. PATENT DOCUMENTS 3,710,283 A    1/1973  Alphonse
4,561,042 A   12/1985  Wehner
(Continued)

FOREIGN PATENT DOCUMENTS

CN    101256277    9/2008
DE     10029147   12/2001
(Continued)

OTHER PUBLICATIONS

International Search Report for PCT International Application No. PCT/US2010/054761, mailed on Jun. 9, 2011, 12 pages.
(Continued)

*Primary Examiner* — David V Bruce
(74) *Attorney, Agent, or Firm* — Daniel J. Iden

(57) ABSTRACT

An illumination device is disclosed, having a lightguide optically coupled to a light source and a transducer for supplying power to the light source by converting energy received from a remote transmitter. Energy received from a remote transmitter can comprise radiofrequency waves, microwaves, infrared radiation, visible light, ultraviolet light, sunlight, sound waves or heat.

8 Claims, 7 Drawing Sheets

(51) Int. Cl.
*G04G 19/00* (2006.01)
*F21V 8/00* (2006.01)
*A44C 5/14* (2006.01)
*A44C 15/00* (2006.01)
*A61N 5/06* (2006.01)
*F21S 9/03* (2006.01)
*F21V 23/00* (2015.01)
*H02J 17/00* (2006.01)

(56) References Cited

U.S. PATENT DOCUMENTS

| | | |
|---|---|---|
| 4,673,896 A | 6/1987 | Brady |
| 5,034,658 A | 7/1991 | Hierig |
| 5,558,422 A | 9/1996 | Sanford |
| 6,096,066 A | 8/2000 | Chen |
| 6,111,696 A | 8/2000 | Allen |
| 6,407,669 B1 | 6/2002 | Brown |
| 7,044,373 B1 | 5/2006 | Garber |
| 7,456,744 B2 | 11/2008 | Kuhns |
| 2003/0004946 A1 | 1/2003 | VanDenAvond |
| 2003/0156431 A1 | 8/2003 | Gozum |
| 2005/0052883 A1 | 3/2005 | Qi |
| 2005/0070976 A1 | 3/2005 | Samuel |
| 2006/0167532 A1 | 7/2006 | Parker |
| 2006/0173514 A1 | 8/2006 | Biel et al. |
| 2006/0206173 A1 | 9/2006 | Gertner |
| 2006/0217787 A1 | 9/2006 | Olson |
| 2006/0289054 A1 | 12/2006 | Iverson |
| 2008/0004510 A1 | 1/2008 | Tanzawa |
| 2008/0074901 A1 | 3/2008 | David |
| 2008/0155965 A1 | 7/2008 | Henderson et al. |
| 2008/0166965 A1* | 7/2008 | Greene .................. H02J 17/00 455/41.1 |
| 2008/0232135 A1 | 9/2008 | Kinder |
| 2008/0290822 A1 | 11/2008 | Greene |
| 2009/0059578 A1 | 3/2009 | Lau |
| 2009/0147523 A1 | 6/2009 | Levon |
| 2010/0161009 A1 | 6/2010 | Forster |

FOREIGN PATENT DOCUMENTS

| | | |
|---|---|---|
| KR | 2006-0010521 | 2/2006 |
| KR | 2007-0079689 | 8/2007 |
| WO | WO 99-41728 | 8/1999 |
| WO | WO 02-21221 | 3/2002 |
| WO | WO 2004-106804 | 12/2004 |
| WO | WO 2006-125174 | 11/2006 |
| WO | WO 2006-133204 | 12/2006 |
| WO | WO 2007-095267 | 8/2007 |
| WO | WO 2010-005655 | 1/2010 |
| WO | WO 2010-005810 | 1/2010 |
| WO | WO 2010-006102 | 1/2010 |
| WO | WO 2010-017087 | 2/2010 |
| WO | WO 2010-151563 | 12/2010 |
| WO | WO 2011-008441 | 1/2011 |
| WO | WO 2011-022525 | 2/2011 |
| WO | WO 2011-088216 | 7/2011 |
| WO | WO 2011-100277 | 8/2011 |
| WO | WO 2012-050663 | 4/2012 |

OTHER PUBLICATIONS

"Sony develops highly efficient wireless power transfer system based on magnetic resonance",Technology / Engineering, Phys.Org, [available on the internet on Oct. 2, 2009], pp. 1-2.

Beierlein, T.A., et al. "RF-Driven OLEDs for Mobile Applications", CSEM, Scientific and Technical Report, 2008, pp. 41.

"The Electromagnetic Spectrum", Hyperphysics, Department of Physics and Astronomy, Georgia State University. [Adapted from hyperphysics.phy-astr.gsu.edu/hbase/ems1.html#c1, on Oct. 28, 2010].

"AM Radio Band", Hyperphysics, Department of Physics and Astronomy, Georgia State University, [Adapted from hyperphysics.phy-astr.gsu.edu/hbase/ems1.html#c1, on Oct. 28, 2010] 7 pages.

* cited by examiner

ILLUMINATION DEVICE HAVING REMOTELY POWERED LIGHTGUIDE

CROSS REFERENCE TO RELATED APPLICATIONS

This application is a continuation of U.S. application Ser. No. 13/501,335, filed on Apr. 11, 2012, which is a national stage filing under 35 U.S.C. 371 of PCT/US2010/054761, filed Oct. 29, 2010, which claims priority to Provisional Application No. 61/263,495, filed on Nov. 23, 2009 and to Provisional Application No. 61/256,827, filed on Oct. 30, 2009, the disclosure of which are incorporated by reference in their entirety herein.

FIELD

This disclosure relates to illumination devices, and particularly to illumination devices having lightguides for facilitating distribution of light emitted by a remotely activated light source.

BACKGROUND

Lightguides are used to facilitate distribution of light from a light source over an area much larger than the light source. Lightguides comprise optically transmissive materials and may have different forms such as slab, wedge, and pseudo-wedge forms. Most lightguides are designed to accept light at an edge surface and allow this light to propagate by total internal reflection between a back surface and an output surface, toward an opposing edge surface from which the light enters. Light is emitted uniformly from the output surface using extracting features that are positioned in various types of patterns on the output surface.

SUMMARY

The illumination device disclosed herein includes a lightguide optically coupled to a light source and a transducer for supplying power to the light source by converting energy received from a remote transmitter. Energy received from a remote transmitter can comprise radiofrequency waves, microwaves, infrared radiation, visible light, ultraviolet light, sunlight, sound waves or heat.

An illumination article comprising the illumination device without the light source is also disclosed herein, as are methods of providing illumination using the illumination device and article.

These and other embodiments of the invention are described in the detailed description below. In no event should the above summary be construed as a limitation on the claimed subject matter which is defined solely by the claims as set forth herein.

BRIEF DESCRIPTION OF DRAWINGS

Advantages and features of the invention may be more completely understood by consideration of the following figures in connection with the detailed description provided below. The figures are schematic drawings of various articles and are not necessarily drawn to scale.

DETAILED DESCRIPTION

Figure 1:
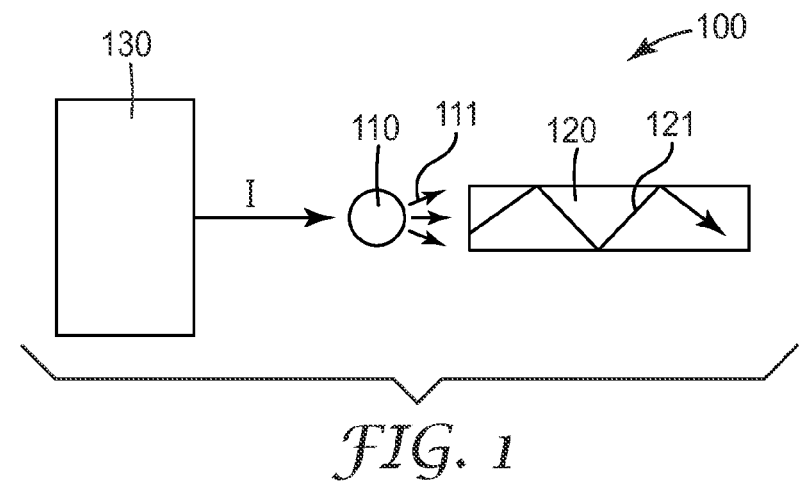
FIG. 1 is a schematic illustration of an exemplary illumination device disclosed herein.

This disclosure relates to U.S. Provisional Application No. 61/256,827 filed on Oct. 30, 2009 and U.S. Provisional Application No. 61/263,495 filed on Nov. 23, 2009 (both to Sherman et al.); WO 2010/005655 A2 (Sherman et al.); PCT/US2010/039577 (Appeaning et al.); U.S. Pat. No. 7,044,373 B1 (Garber et al.); U.S. Pat. No. 6,407,669 B1 (Brown et al.); U.S. Pat. No. 7,456,744 B2 (Kuhns et al.); and US2003/0004946 A1 (VanDenAvond et al.); the disclosures of which are incorporated by reference herein.

As described in the above-cited Sherman et al. references, light sources and lightguides can be used to transform everyday articles such as watches, labels and medical devices into illuminated versions of these articles. However, the light sources are powered by some external power supply which, in many cases, cannot be readily incorporated into such articles or if incorporated, imposes limitations on the design of the articles.

The ability to power optical sources remotely could impact many lighting applications such as labels, security and medical devices, and organizers/containers. Lighted ceiling panels for drop ceilings could be RF (radio frequency) powered from a ceiling grid so that if full contact with the "wired" grid were not possible, or if tiles of the grid became misaligned, the lighting would still function without the need for physical contact. If the RF power supply included an identification portion, typically referred to as radio frequency identification (RFID) technology, it could be possible to obtain various types of information from an illuminated article beyond the usual "track and trace" for which RFID technology is used. For example, RFID technology could be used to provide information such as a burned out light source or when a light source draws too much power from a power supply. Additionally, RFID technology could be used to advertise products, and for systems such as those used in libraries, could be set up to identify collection of purchase fees. This offers the store owner and the consumer benefits at the same time in the same part.

This invention describes ways to power a light source, such as a light emitting diode (LED), from a power supply located in either a separate part of an illuminated article or remotely with no physical connection to an article to be illuminated. The invention may be achieved by providing a physical conductive path to transport power to different parts of an article, or by providing means to transport power wirelessly using induction power.

Faraday's law states that a time-varying magnetic field through a surface bounded by a closed path or loop induces a voltage around the loop. When a power supply antenna is in close proximity to a closed antenna coil, a time-varying magnetic field is generated which induces a voltage (called electromotive force or EMF) in the closed antenna coil such that a flow of current is produced on the coil. A light source connected to the closed antenna coil can provide illumination if connected to the closed antenna coil. For example, as described in Example 1, if an illuminated watchband as a decorative feature if desired, the light source could be incorporated into the watchband, and the power supply for the light source in the watch body. The power supply could comprise the battery used to power the watch.

Illuminated labels with brand markings can be made as described in Example 2, wherein a viscoelastic lightguide is incorporated into a construction of the label on a can. Light sources such as LEDs can be powered from remote places when the cans are displayed on a store shelf which can attracting the attention of customers.

Light sources such as LEDs can be RF powered by rapid pulsation of RF signals such that the LEDs appear to glow, and intermittent pulsation can be used to make the LEDs blink. Colored light sources can be powered using LEDs which utilize different voltages for color, and colors can be added or changed with an increase or decrease in signal strength. It is also envisioned that if two or more RF circuits are utilized in a system, each circuit having a different color, a watch or label could pulse one or more of the light sources forming patterns, color changing, etc.

Viscoelastic lightguides such as pressure sensitive adhesive (PSA) lightguides could be used to bond labels to substrates of bottles, such as a green LED label on a green Prell™ Shampoo bottle or blue LEDs on a bottle of Dawn™ dishwashing liquid. A viscoelastic lightguide could allow for light extraction when bonded to such substrates, and the labels and/or product could be made to glow using ultraviolet (UV) LEDs or fluorescent compounds in the bottles. Light would be extracted back into the bottle by attaching the label to the bottle using a viscoelastic lightguide.

Selected areas of labels can be illuminated by incorporating UV LEDs or phosphor pigment in the selected areas while other areas remain dark. As a result, labels with improved contrast and color brightness can be obtained.

The invention can also be used in medical devices and treatments, such as for antimicrobial purposes, basic skin optical and drug delivery (such as with IR LEDs). Devices include the light-activated antimicrobial device described in Appening et al which comprises a light source and a light-activated antimicrobial article comprising a photosensitizer and a viscoelastic lightguide. The use of remotely powered lightguides in conjunction with bandages and dressings can improve the ease by which the devices can be applied, as well as reduce the risk of infection associated with the use of bulky wires.

FIG. 1 is a schematic illustration of an exemplary illumination device according to some embodiments of the invention. Illumination device 100 comprises light source 110, lightguide 120 and transducer 130. Light source 110 is positioned relative to lightguide 120 such that light emitted by the light source and represented by rays 111 enters the lightguide. Light within lightguide 120 and represented by single ray 121 is transported within the lightguide by total internal reflection. Transducer 130 comprises a power source that induces current, I, to power light source 110.

Figure 2A:
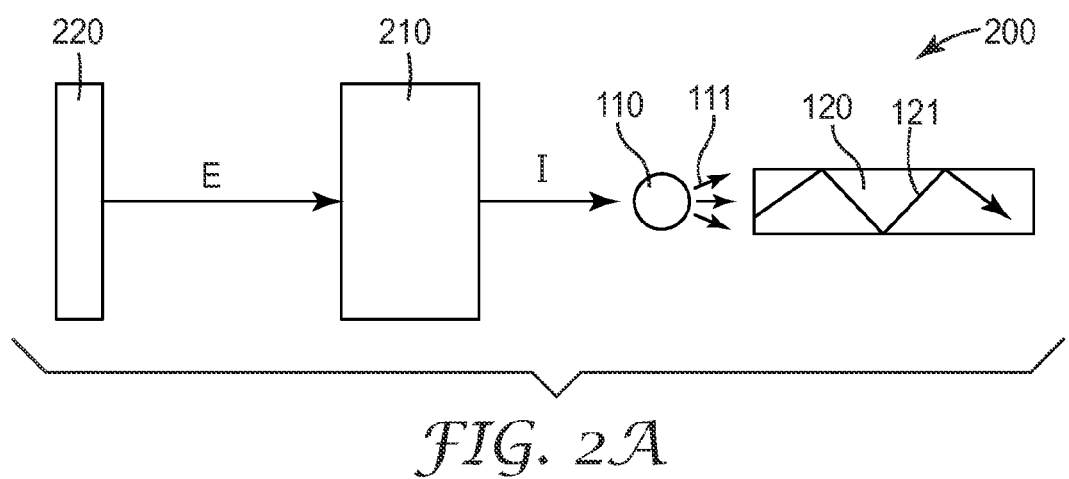
FIGS. 2a-b, 3a-b and 4-9 are schematic illustrations of exemplary illumination devices receiving power from a remote transmitter.

FIG. 2a is a schematic illustration of an exemplary illumination device according to some embodiments of the invention. Illumination device 200 comprises transducer 210 that induces current, I, to power light source 110. Transducer 210 comprises a receiver that receives energy, E, from transmitter 220. In this embodiment, the receiver and transmitter are local to each other meaning that they are physically connected.

Figure 2B:
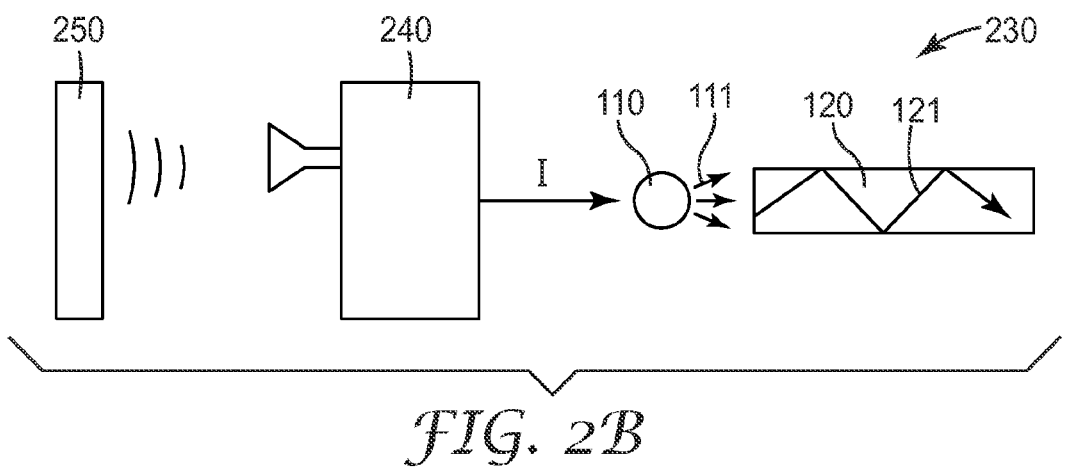

FIG. 2b is a schematic illustration of an exemplary illumination device according to some embodiments of the invention. Illumination device 230 comprises transducer 240 that induces current, I, to power light source 110. Transducer 240 comprises a receiver that receives energy, E, from remote transmitter 250. In this embodiment, the receiver and transmitter are remote to each other meaning that they are not physically connected.

The transducer is a device that converts some form of input energy into electrical energy such that power is supplied to the light source. The transducer comprises an energy input device or receiver in combination with a circuit. The transducer can convert electromagnetic, mechanical, thermal, or chemical energy into electrical energy. The transducer is typically a receiver for receiving input energy but can be any device which converts energy into electrical signals. The transducer can be configured to receive energy by induction. The transducer may comprise transparent conductor, transparent polymer, metal, conductive metal, conductive polymer, or a combination thereof.

The remote transmitter used in the invention generally comprises a power source. Any type of power source can be used, as long as the remote transmitter is able to provide the necessary energy to the transducer that powers the light source. The remote power source may generate, for example, electromagnetic energy, kinetic energy and/or chemical energy. Types of electromagnetic energy include UV and visible light, heat, radiowaves, and microwaves. Remote power sources that may be used to generate electromagnetic energy include an energy transmitting portion, a circuit and a remote power source.

Figure 3A:
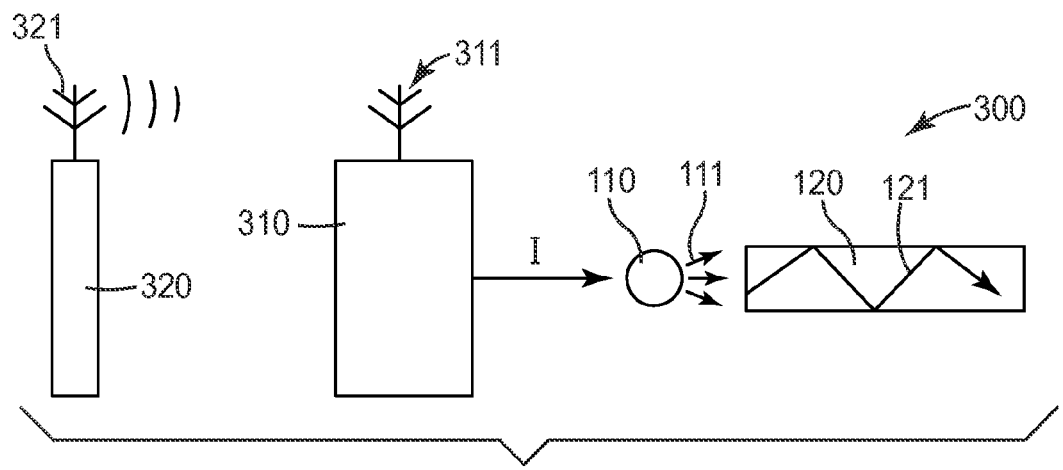

The transducer is configured to power the light source using input energy received from the remote transmitter. In some embodiments, the input energy comprises electromagnetic radiation. The input energy can comprise electromagnetic radiation used for telecommunications, referred to herein as radiofrequency (RF) waves, which includes AM and FM radio waves, short wave radio waves, and television waves. RF waves can have a frequency of greater than $10^5$ m to less than $10^9$ Hz. An appropriate transducer comprises a receiving antenna for receiving the RF waves and a device for converting the waves into electrical signals. FIG. 3a is a schematic illustration of an exemplary illumination device used in conjunction with a remote transmitter comprising a transmitting antenna. Illumination device 300 comprises transducer 310 that induces current, I, to power light source 110. Transducer 310 comprises receiving antenna 311 for receiving electromagnetic waves from remote transmitter 320 comprising transmitting antenna 321.

An RF tag such as those used in RFID technology can be used as the receiver. The RF tag can be responsive to a particular radio frequency such that the tag can power up itself and respond by radiowave to communicate information such as a SKU indentifier. For example, a control system can provide energy to power up the RF tag and make a query by sending out RF waves using an antenna. The RF tag may be an intelligent device, comprising a programmed chip used in combination with a circuit.

The remote transmitter may transmit electromagnetic radiation. Examples include the 3M™ RFID Tracking Pad that is available from 3M™ Co.; shelving or other components used in "smart shelf" technology; and a cell phone or other handheld electronic device.

In some embodiments, the input energy comprises microwaves having a frequency of greater than 1000 to 30,000 MHz. Microwaves can be generated in electronic devices that produce oscillations at microwave frequencies. The devices may be single-frequency or tunable, and continuous-wave or pulsed. Microwaves can be generated using a gyrotron, klystron, magnetron, backward-wave oscillator, solid-state generator such as a tunnel diode, Gunn diode, IMPATT diode, transistor oscillator, maser, and harmonic generators using varactor diodes. Transmitters for microwaves include cell phone towers. Receivers for microwaves include antennas. Transducers for converting microwaves into electrical signals include semiconductors. One example of a semiconductor comprises a PIN diode as described in U.S. Pat. No. 4,673,896 (Brady et al.). Transducers for converting microwaves are also described in U.S. Pat. No. 3,710,283 (Alphonse).

In some embodiments, the input energy comprises infrared (IR) radiation, from the near IR to the far IR frequencies, having a frequency of greater than $10^{10}$ to about $5 \times 10^{14}$ Hz. Transducers for converting IR radiation into electrical signals include photodetectors including photodiodes, and materials which exhibit the pyroelectric effect such as pyroelectric crystals. Remote transmitters for transmitting IR radiation include LEDs that emit IR radiation. Other IR detectors include silicon photodiodes and silicon photocells. IR remote controls can also be used.

In some embodiments, the input energy comprises visible and/or UV light, having a wavelength of about 200 nm to about 800 nm. Transducers for converting visible light and/or UV light include photovoltaic cells, photodetectors including photodiodes. Remote transmitters for transmitting visible and UV light include any of those described below for the light sources of the illumination device.

Figure 3B:
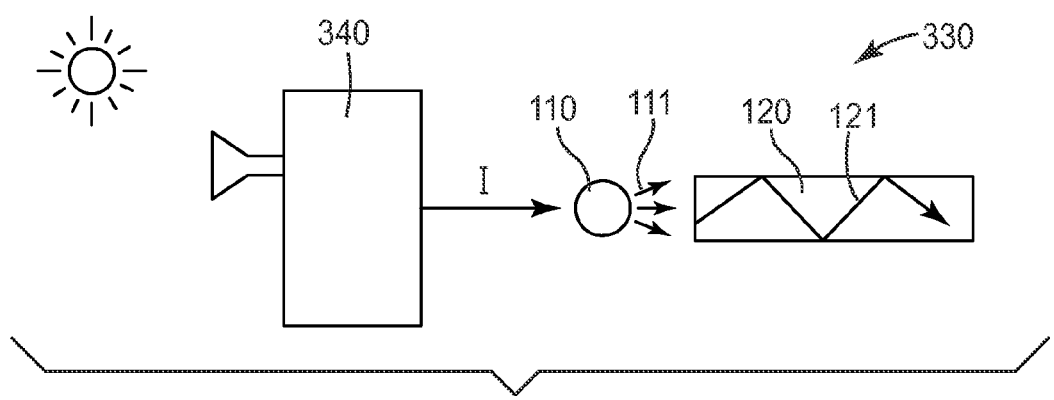

Input energy can be obtained from the sun. FIG. 3b is a schematic illustration of an exemplary illumination device according to some embodiments of the invention. Illumination device 330 comprises transducer 340 that induces current, I, to power light source 110. Transducer 340 comprises a solar cell or photovoltaic cell for receiving and converting energy from the sun.

The input energy can comprise kinetic energy used in conjunction with a motion transducer. Kinetic energy, such as kinetic energy resulting from an applied mechanic force, can be in the form of sound waves (about 1 to about 25,000 kHz). For example, the transducer may comprise a microphone for receiving sound waves. Remote transmitters for transmitting sound waves include loudspeakers. Materials which exhibit the piezoelectric effect, such as piezoelectric crystals, can also be used as motion transducers. Remote transmitters for generating kinetic energy received by the motion transducer include people and animals in motion; and wind gathering devices such as windmills (wind power). Other sources of kinetic energy include wave action from water (hydro power), vibration from mechanical sources, combustion turbines, vibration from roads, railroads, fixed or moving engines. Kinetic energy can be obtained by converting chemical potential energy such as with combustion of hydrocarbons, coal and other fuels.

The input energy can comprise heat used in conjunction with a thermal transducer. Materials which exhibit the pyroelectric effect, such as pyroelectric crystals, can be used as thermal transducers. Thermopiles can convert thermal energy into electrical energy and are comprised of electronically coupled thermocouples which can generate an output voltage proportional to a local temperature difference or temperature gradient.

The input energy can comprise chemical energy. Remote power sources that may be used to generate chemical energy include fuel cells and batteries.

The remote power source may be a local power company. The remote power source may produce AC or DC power. AC sources include nuclear energy, coal, a generator, etc. DC sources include solar cells, batteries, USB communication, etc.

Figure 4:
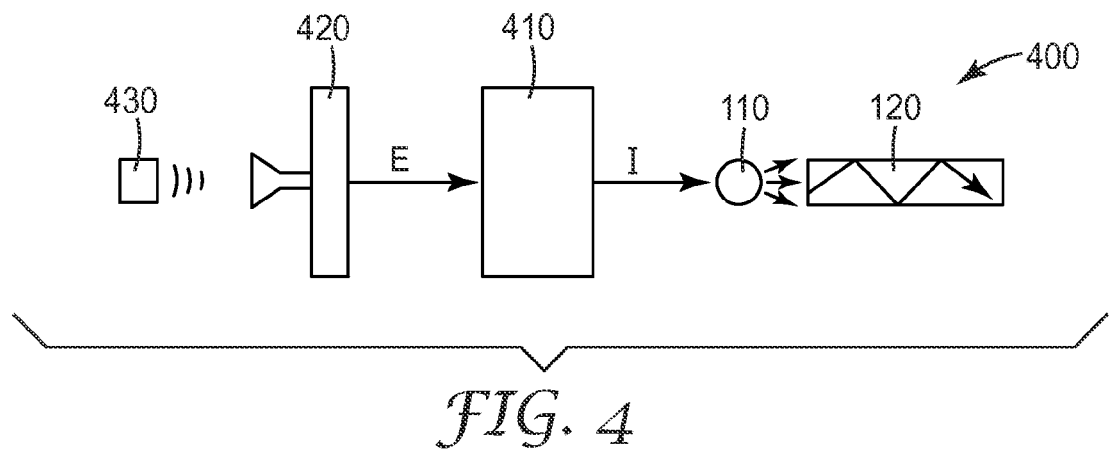

FIG. 4 is a schematic illustration according to some embodiments of the invention. Illumination device 400 comprises light source 110, lightguide 120, and first transducer 410 that induces current, I, to power light source 110. First transducer 410 receives first energy, E, from second transducer 420 which can be either remote or local as shown in FIG. 4. Second transducer 420 receives second energy from remote transmitter 430. Remote transmitter 430 can be either remote as shown in FIG. 4, or it can be local. The first transducer can comprise any of the transducers described above for converting input energy into electrical energy used to power the light source. The second transducer is not limited to any particular type of transducer, rather, the second transducer can be any type of transducer that converts second energy received from the remote transmitter to first energy received by the first transducer.

Figure 5:
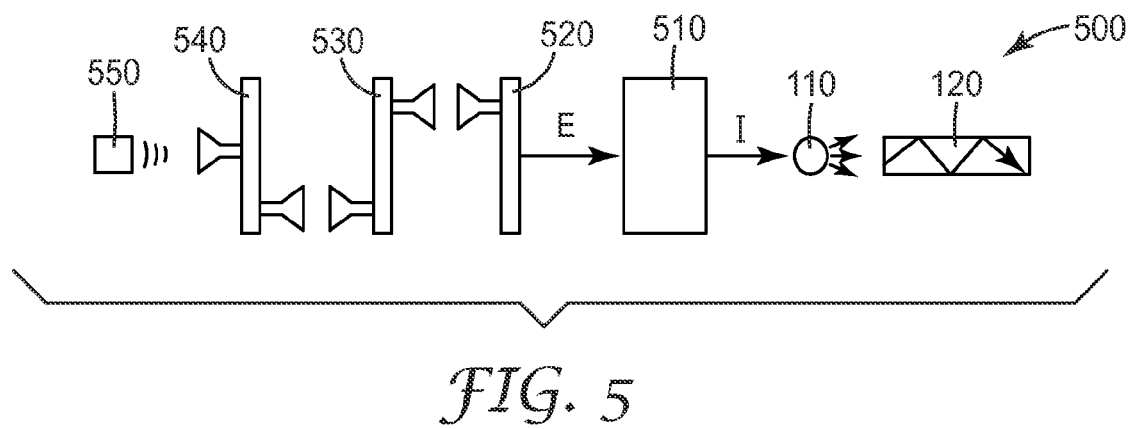

FIG. 5 is a schematic illustration according to some embodiments of the invention. Illumination device 500 comprises light source 110, lightguide 120, and first transducer 510 that induces current, I, to power light source 110. First transducer 510 receives first energy, E, from second transducer 520 which can be either remote or local as shown in FIG. 5. Second transducer 520 receives second energy from third transducer 530 which can be either local or remote as shown in FIG. 5. Third transducer 530 receives third energy from fourth transducer 540 which can be either local or remote as shown in FIG. 5. Remote transmitter 550 can be either remote as shown in FIG. 5, or it can be local. Each of the second, third and fourth transducers can be any type of transducer as long as they are matched as described above for FIG. 4.

Figure 6:
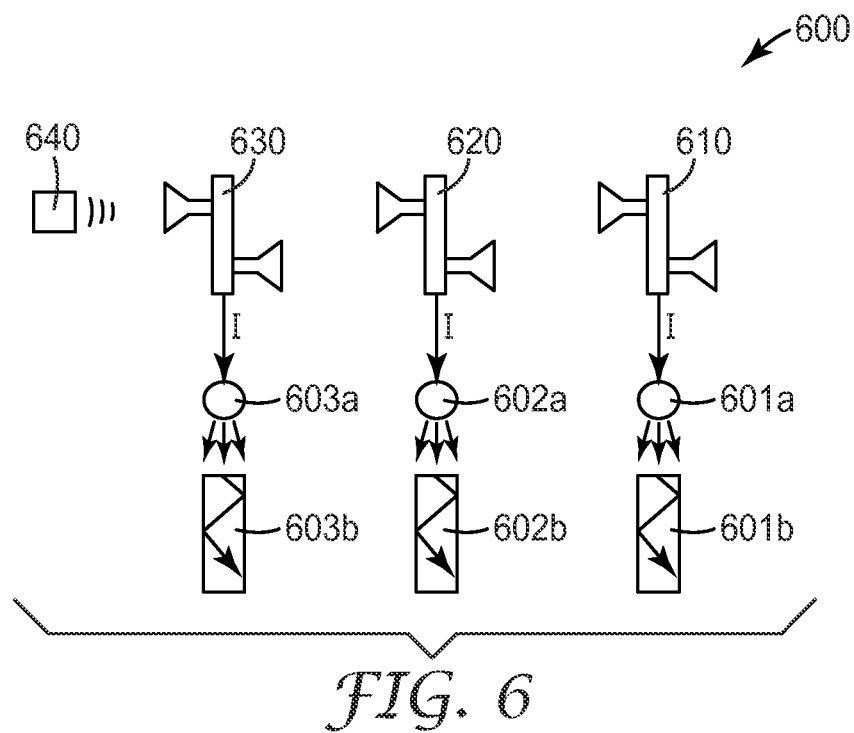

FIG. 6 is a schematic illustration according to some embodiments of the invention. Illumination device 600 comprises light sources 601a, 602a and 603a, and corresponding lightguides 601b, 602b and 603b, respectively. Illumination device 600 also comprises transducers 610, 620 and 630, each capable of receiving energy transmitted by remote transmitter 640. In this embodiment, energy transmitted by a remote transmitter is received by more than one transducer, each transducer configured to supply power to a light source.

Figure 7:
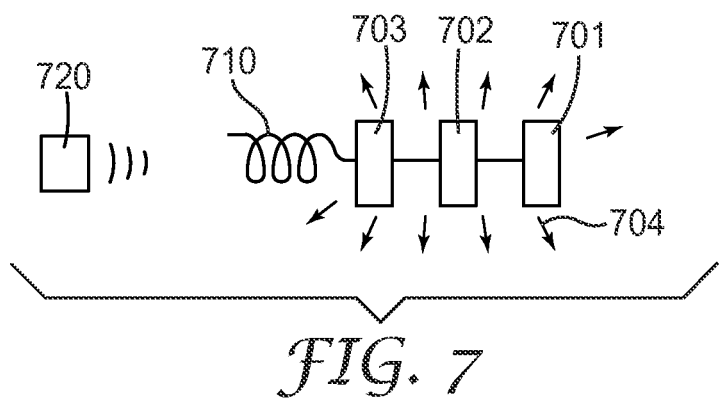

FIG. 7 is a schematic illustration of an embodiment of the invention. Illumination device 700 comprises light sources 701, 702 and 703 connected in series as shown in FIG. 7. Transducer with antenna 710 receives energy transmitted by remote transmitter 720. In this embodiment, energy transmitted by a remote transmitter is received by a transducer configured to supply power to more than one light source connected in series.

Figure 8:
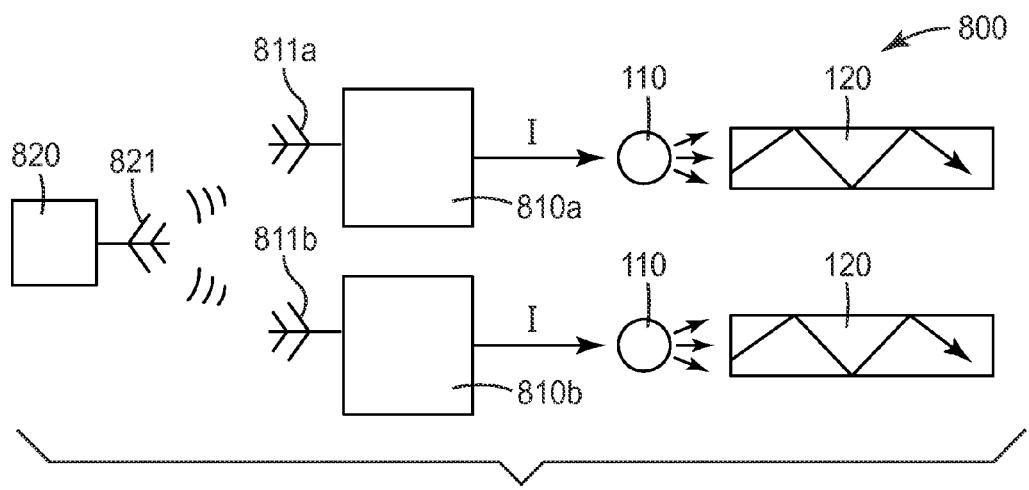

FIG. 8 is a schematic illustration according to some embodiments of the invention. Illumination device 800 comprises light sources 110, lightguides 120, first transducer 810a comprising first receiving antenna 811a, and second transducer 810b comprising second receiving antenna 811b. Remote transmitter 820 comprises transmitting antenna 821 for transmitting RF waves which are received by the first and second receiving antennas. In this embodiment, RF waves are transmitted from a remote transmitter, and the RF waves are received by more than one transducer, each transducer configured to supply power to a light source.

Figure 9:
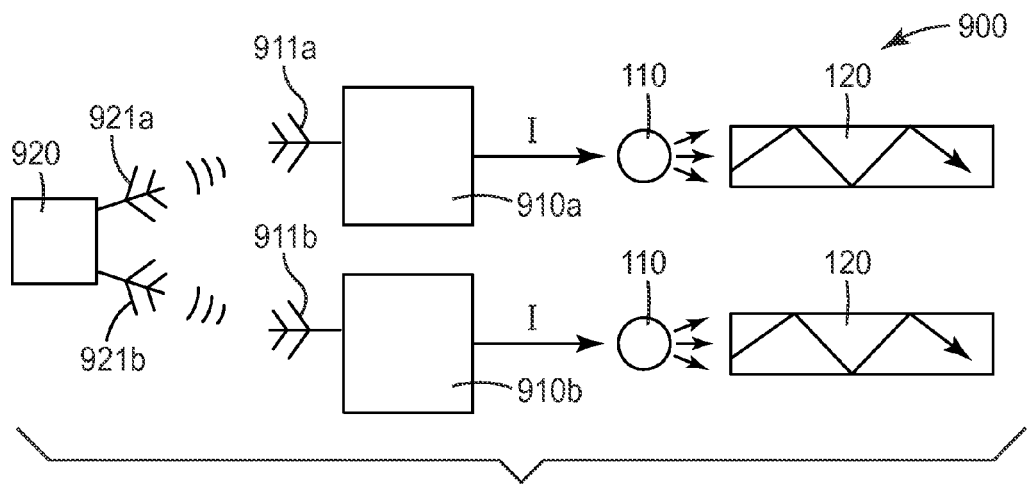

FIG. 9 is a schematic illustration according to some embodiments of the invention. Illumination device 900 comprises light sources 110, lightguides 120, first transducer 910a comprising first receiving antenna 911a, and second transducer 910*b* comprising second receiving antenna 911*b*. Remote transmitter 920 comprises transmitting antennas 921*a* and 921*b* for transmitting RF waves of different frequencies which are received by the first and second receiving antennas. In this embodiment, RF waves of different frequencies are transmitted from a remote transmitter, and the RF waves of each frequency are received by different transducers, each transducer configured to supply power to a light source.

The illumination device disclosed herein comprises a lightguide and a light source. Light is emitted by the light source, enters the lightguide, and propagates, reflects, and/or refracts according to the law of refraction and the principle of total internal reflection. The behavior of light within the lightguide may depend on a variety of factors such as the surface structure of the lightguide, the presence (or absence) of additional substrate(s) in contact with the lightguide, and/or the material compositions of the lightguide and any additional substrate(s) in contact with the lightguide. In addition, the behavior of light within the lightguide may depend on the angular distribution of light that enters the lightguide.

The behavior of light with respect to the illumination devices disclosed herein can be described using principles of geometric optics. These principles are well known and are not presented here; a more detailed description can be found in the Sherman et al. references cited above. In general, one may apply the law of refraction and the principle of total internal reflection in conjunction with ray tracing techniques to determine theoretically how varying three dimensional structure, material composition, layer construction, angular distribution of light, etc. can affect the behavior of light for the illumination devices and articles disclosed herein.

The lightguide may have a refractive index greater than about 0.01, greater than about 0.1, or greater than about 0.5. When an optical article for managing light (such as an extractor) is disposed adjacent the lightguide, the refractive index difference between the lightguide and the optical article may be from about 0.002 to about 0.5, from about 0.02 to about 0.5, from about 0.05 to about 0.5, from about 0.1 to about 0.5, or from about 0.4 to about 0.5.

The lightguide may have any bulk three-dimensional shape as is needed for a given application. The lightguide may be in the form of a square or rectangular layer, sheet, film, etc. The lightguide may be cut or divided into shapes as described below.

The thickness of the lightguide is not particularly limited as long as it can function as desired. The thickness of the lightguide may be selected based on or in conjunction with the light source. Exemplary thicknesses for the lightguide range from about 0.4 mil to about 1000 mil, from about 1 mil to about 300 mil, from about 1 mil to about 60 mil, or from about 0.5 mil to about 30 mil.

The amount and direction of light extracted from the lightguide may be controlled, at the very least, by the shape, size, number, arrangement, etc. of the features, the refractive indices of the lightguide and any medium with which the lightguide is in contact, the shape and size of the lightguide, and the angular distribution of light that is allowed to enter the lightguide. These variables may be selected such that from about 10 to about 50%, from about 20 to about 50%, from about 30 to about 50%, from about 50 to about 70%, from about 50 to about 80%, or from about 10 to about 90% of light is extracted from the lightguide relative to the total amount of light that enters the lightguide.

In some embodiments, the lightguide is a viscoelastic lightguide comprising one or more viscoelastic materials. In general, viscoelastic materials exhibit both elastic and viscous behavior when undergoing deformation. Elastic characteristics refer to the ability of a material to return to its original shape after a transient load is removed. One measure of elasticity for a material is referred to as the tensile set value which is a function of the elongation remaining after the material has been stretched and subsequently allowed to recover (destretch) under the same conditions by which it was stretched. If a material has a tensile set value of 0%, then it has returned to its original length upon relaxation, whereas if the tensile set value is 100%, then the material is twice its original length upon relaxation. Tensile set values may be measured using ASTM D412. Useful viscoelastic materials may have tensile set values of greater than about 10%, greater than about 30%, or greater than about 50%; or from about 5 to about 70%, from about 10 to about 70%, from about 30 to about 70%, or from about 10 to about 60%.

Viscous materials that are Newtonian liquids have viscous characteristics that obey Newton's law which states that stress increases linearly with shear gradient. A liquid does not recover its shape as the shear gradient is removed. Viscous characteristics of useful viscoelastic materials include flowability of the material under reasonable temperatures such that the material does not decompose.

The viscoelastic lightguide may have properties that facilitate sufficient contact or wetting with at least a portion of a material designed to extract light from the lightguide, e.g., an optical article, such that the viscoelastic lightguide and the optical article are optically coupled. Light can then be extracted from the viscoelastic lightguide. The viscoelastic lightguide is generally soft, compliant and flexible. Thus, the viscoelastic lightguide may have an elastic modulus (or storage modulus G') such that sufficient contact can be obtained, and a viscous modulus (or loss modulus G") such that the layer doesn't flow undesirably, and a damping coefficient (G"/G', tan D) for the relative degree of damping of the layer. Useful viscoelastic materials may have a storage modulus, G', of less than about 300,000 Pa, measured at 10 rad/sec and a temperature of from about 20 to about 22° C. Viscoelastic properties of materials can be measured using Dynamic Mechanical Analysis according to, for example, ASTM D4065, D4440, and D5279.

In some embodiments, the viscoelastic lightguide comprises a PSA layer as described in the Dalquist criterion line (as described in Handbook of Pressure Sensitive Adhesive Technology, Second Ed., D. Satas, ed., Van Nostrand Reinhold, New York, 1989.)

The viscoelastic lightguide may have a particular peel force or at least exhibit a peel force within a particular range. For example, the viscoelastic lightguide may have a 90° peel force of from about 50 to about 3000 W/in, from about 300 to about 3000 g/in, or from about 500 to about 3000 g/in. Peel force may be measured using a peel tester from IMASS.

In some embodiments, the viscoelastic lightguide comprises an optically clear lightguide having high light transmittance of from about 80 to about 100%, from about 90 to about 100%, from about 95 to about 100%, or from about 98 to about 100% over at least a portion of the visible light spectrum (about 400 to about 700 nm). In some embodiments, the viscoelastic lightguide has a haze value of less than about 5%, less than about 3%, or less than about 1%. In some embodiments, the viscoelastic lightguide has a haze value of from about 0.01 to less than about 5%, from about 0.01 to less than about 3%, or from about 0.01 to less than about 1%. Haze values in transmission can be determined using a haze meter according to ASTM D1003.

In some embodiments, the viscoelastic lightguide comprises an optically clear lightguide having high light transmittance and a low haze value. High light transmittance may be from about 90 to about 100%, from about 95 to about 100%, or from about 99 to about 100% over at least a portion of the visible light spectrum (about 400 to about 700 nm), and haze values may be from about 0.01 to less than about 5%, from about 0.01 to less than about 3%, or from about 0.01 to less than about 1%. The viscoelastic lightguide may also have a light transmittance of from about 50 to about 100%.

In some embodiments, the viscoelastic lightguide is hazy and diffuses light, particularly visible light. A hazy viscoelastic lightguide may have a haze value of greater than about 5%, greater than about 20%, or greater than about 50%. A hazy viscoelastic lightguide may have a haze value of from about 5 to about 90%, from about 5 to about 50%, or from about 20 to about 50%.

In some embodiments, the viscoelastic lightguide may be translucent in that it reflects and transmits light.

The viscoelastic lightguide may have a refractive index in the range of from about 1.3 to about 2.6, 1.4 to about 1.7, or from about 1.5 to about 1.7. The particular refractive index or range of refractive indices selected for the viscoelastic lightguide may depend on the overall design of the illumination device and the particular application in which the device may be used.

The viscoelastic lightguide generally comprises at least one polymer. The viscoelastic lightguide may comprise at least one PSA. PSAs are useful for adhering together adherends and exhibit properties such as: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process. A quantitative description of PSAs can be found in the Dahlquist reference cited above.

Useful PSAs are described in detailed in the Sherman et al. references cited above. Useful PSAs include poly(meth)acrylate PSAs derived from: monomer A comprising at least one monoethylenically unsaturated alkyl (meth)acrylate monomer, wherein a homopolymer of the monomer has a Tg of no greater than about 0° C.; and monomer B comprising at least one monoethylenically unsaturated free-radically copolymerizable reinforcing monomer, wherein a homopolymer of the monomer has a Tg higher than that of monomer A, for example, at least about 10° C. As used herein, (meth)acrylic refers to both acrylic and methacrylic species and likewise for (meth)acrylate.

In some embodiments, the viscoelastic lightguide comprises natural rubber-based and synthetic rubber-based PSAs, thermoplastic elastomers, tackified thermoplastic-epoxy derivatives, polyurethane derivatives, polyurethane acrylate derivatives, silicone PSAs such as polydiorganosiloxanes, polydiorganosiloxane polyoxamides and silicone urea block copolymers.

In some embodiments, the viscoelastic lightguide comprises a clear acrylic PSA, for example, those available as transfer tapes such as VHB™ Acrylic Tape 4910F from 3M Company and 3M™ Optically Clear Laminating Adhesives (8140 and 8180 series).

In some embodiments, the viscoelastic lightguide comprises a block copolymer dispersed in an adhesive matrix to form a Lewis acid-base pair. In some embodiments, the viscoelastic lightguide comprises a stretch releasable PSA that can be removed from a substrate when stretched at or nearly at a zero degree angle.

The viscoelastic lightguide can optionally include one or more additives such as filler, particles, fibers, bubbles, plasticizers, chain transfer agents, initiators, antioxidants, stabilizers, fire retardants, viscosity modifying agents, foaming agents, antistats, colorants such as dyes and pigments, fluorescent dyes and pigments, phosphorescent dyes and pigments, fibrous reinforcing agents, and woven and nonwoven fabrics.

The light source may be optically coupled to the lightguide such that at least some of the light from the light source can enter the lightguide. For example, a light source may be optically coupled to the lightguide such that greater than 1, greater than 10, greater than 20, greater than 30, greater than 40, greater than 50, greater than 90%, or about 100% of light emitted by the light source enters the lightguide. For another example, a light source may be optically coupled to the lightguide such that from about 1 to about 10%, from about 1 to about 20%, from about 1 to about 30%, from about 1 to about 40%, from about 1 to about 50%, from about 1 to about 100%, from about 1 to about 100%, from about 50 to about 100%, or from about 1 to about 100% of light emitted by the light source enters the lightguide. The light source may emit light having a random or a particular angular distribution.

The light source may comprise any suitable light source. Exemplary light sources include linear light sources such as cold cathode fluorescent lamps and point light sources such as light emitting diode (LEDs). Exemplary light sources also include organic light-emitting devices (OLEDs), incandescent bulbs, fluorescent bulbs, halogen lamps, UV bulbs, infrared sources, near-infrared sources, lasers, or chemical light sources. In general, the light emitted by the light source may be visible or invisible. At least one light source may be used. For example, from 1 to about 10,000 light sources may be used. The light source may comprise a row of LEDs positioned at or near an edge of the lightguide. The light source may comprise LEDs arranged on a circuit such that light emitted from the LEDs lights up continuously or uniformly the lightguide throughout a desired area. The light source may comprise LEDs that emit light of different colors such that the colors can mix within the lightguide. In this way, a graphic could be designed to appear differently at different times during its use.

Figure 10:
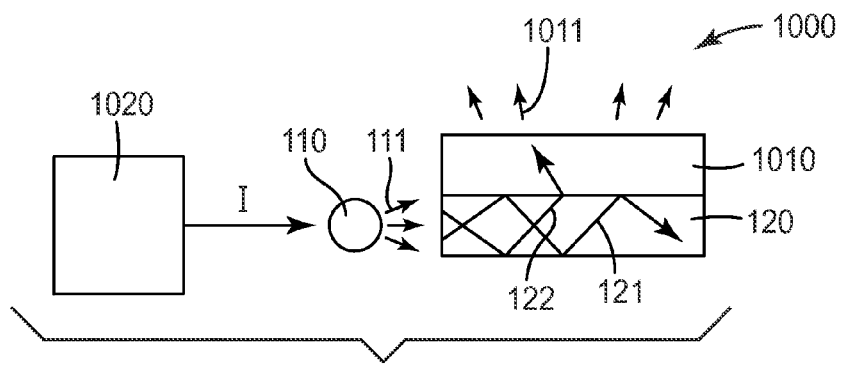
FIG. 10 is a schematic illustration of an exemplary illuminated article comprising an exemplary illumination device.

FIG. 10 is a schematic illustration of an exemplary illumination device according to some embodiments of the invention. Illumination device 1000 comprises light source 110, lightguide 120, extractor 1010 optically coupled to the lightguide, and transducer 1020. Light source 110 is positioned relative to lightguide 120 such that light emitted by the light source and represented by rays 111 enters the lightguide. Light within lightguide 120 and represented by single ray 121 is transported within the lightguide by total internal reflection. Light within lightguide 120 and represented by single ray 122 is transported within the lightguide by total internal reflection and extracted into extractor 1010. Transducer 1020 is a power source that induces current, I, to power light source 110.

The extractor may comprise any type of article that can be optically coupled to the lightguide. The extractor is typically selected according to the intended use of the illumination device. The illumination devices may be used in many different types of applications as described in WO 2010/005655 A2 (Sherman et al.), and a brief description is included here. The illumination devices may be used for signage such as for graphic arts applications, and on or in windows, walls, wallpaper, wall hangings, pictures, posters, billboards, pillars, doors, floormats, vehicles, or anywhere signage is used.

The illumination devices may be used for safety purposes wherever light is desired. For example, the illumination devices may be used to illuminate one or more steps of a ladder, steps of a stairway, aisles such as in airplanes and movie theatres, walkways, egress, handrails, work zone identification signs and markings.

The illumination devices may be used in a variety of items such as reading lights; party and holiday decorations such as hats, ornaments, string lighting, balloons, gift bags, greeting cards, wrapping paper; desk and computer accessories such as desk mats, mousepads, notepad holders, writing instruments; sporting items such as fishing lures; craft items such as knitting needles; personal items such as toothbrushes; household and office items such as clock faces, wall plates for light switches, hooks, tools.

The illumination devices may be used on clothing and clothing accessories for decorative and/or safety purposes such as on outerwear for cyclists, on clothing or headgear for miners. The illumination devices may be used in wristbands and watch bodies as described below in Example 1 and corresponding FIGS. 11a-b.

The illumination devices may be used anywhere light is needed or desired, e.g., on a top or bottom surface of a shelf, or within a shelf having a light transmissive portion. The illumination devices may be used as flashlights, e.g., they can be disposed on the outside or inside of a battery cover plate or other part of an electronic handheld device.

The illumination devices may be used with vehicles such as automobiles, marine vehicles, buses, trucks, railcars, trailers, aircraft, and aerospace vehicles. The illumination devices may be used on almost any surface of a vehicle including the exterior, interior, or any in-between surface, e.g., to light up door handles on the exterior and/or interior of a vehicle, or to illuminate trunk compartments, bumpers, spoilers, floor boards, windows, instrument panels, on or as tail lights, sill plate lights, puddle lights, emergency flashers, center high mounted stop lights, side lights and markers, engine compartments, between the exterior and interior panels of the doors, on cupholders and seats, and the like.

The illumination devices may be used for traffic safety such as for traffic signs, street signs, highway dividers and barriers, toll booths, pavement markings, and work zone identification signs and markings, on license plates for decoration, or to provide information such as vehicle registration, etc. The illumination devices may also be used to provide light near license plates such that the license plates are lit up from the side, top, etc.

The illumination devices may be used with optical devices comprising hollow light recycling cavities sometimes referred to as backlight assemblies. Backlight assemblies may be used for signage or general lighting. Exemplary backlight assemblies are disclosed in WO 2006/125174 (Hoffman et al.) and US 2008/0074901 (David et al.) all incorporated herein by reference. The illumination devices disclosed herein may be used to replace the light sources described in these references.

The illumination devices may be used on or in display devices such as cell phones, personal digital devices, MP3 players, digital picture frames, monitors, laptop computers, projectors such as mini-projectors, global positioning displays, televisions, etc. The illumination articles may be used in place of conventional lightguides used to backlight a display panel of the display device such as those having LCD and plasma display panels. Exemplary display devices are described in US 2008/232135 A1 (Kinder et al.) and U.S. Pat. No. 6,111,696 (Allen et al.). The illumination devices may also be used for lighting buttons and keypads in various electronic devices including such display devices.

The illumination devices disclosed herein may be incorporated into security films or laminates used to make driver licenses, passports, tamper proof seals and the like, and in the construction of illuminated license plates. The illumination devices disclosed herein may be used for creating three-dimensional (3D) images in displays, buttons, keypads and the like.

The illumination devices disclosed herein may be used in sensing/detecting devices wherein a sensor is disposed to receive light emitted from the viscoelastic lightguide. Also disclosed is a sensing/detecting device in which the light source is replaced with a sensor/detector. The sensor/detector can be a photodetector, a silicon photodiode, an IR detector, a solar cell, or an optoelectronic device, or some combination thereof The illumination devices disclosed herein may be incorporated into a therapeutic device. For example, the optical articles and devices disclosed herein may be used in conformal patches for providing light therapy to tissue. Exemplary conformal patches are described in U.S. Pat. No. 6,096,066 (Chen et al.), incorporated herein by reference. Additional therapeutic devices are described in U.S. 2005/0070976 A1 (Samuel et al.); *Electronics World,* October 2007; and *LEDs Magazine,* November 2006; all of which are incorporated herein by reference.

The terms "in contact" and "disposed on" are used generally to describe that two items are adjacent one another such that the whole item can function as desired. This may mean that additional materials can be present between the adjacent items, as long as the item can function as desired.

EXAMPLES

Example 1

Illuminated Watchbands

Figure 11A:
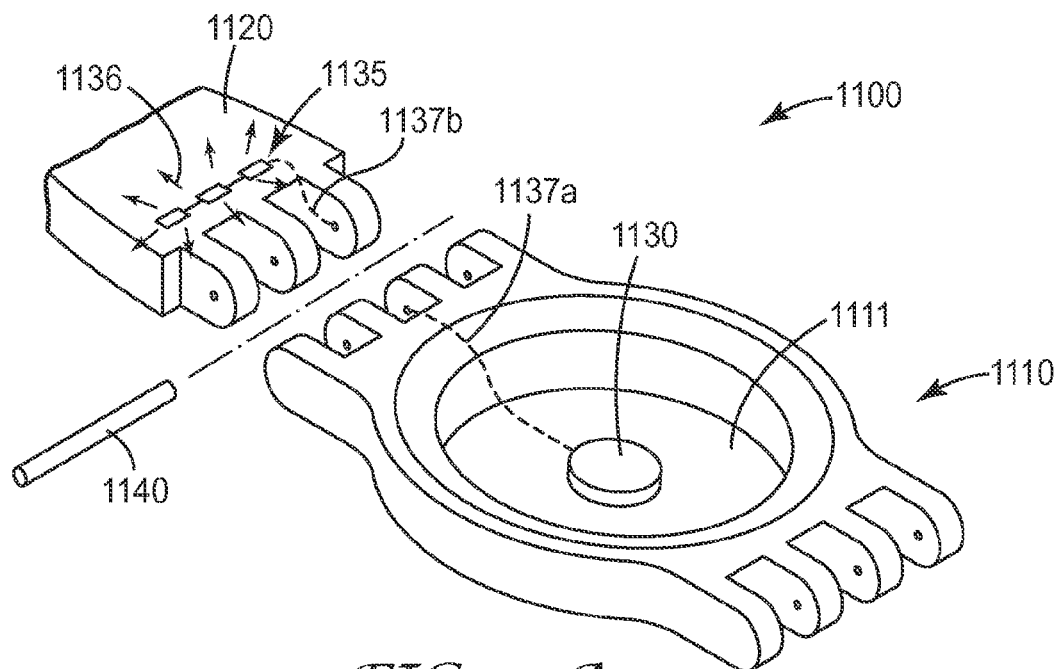
FIGS. 11a-b are schematic illustrations of watches comprising exemplary illumination devices.

FIGS. 11a shows a schematic drawing of watch 1100 comprising body 1110 and illuminated watchband 1120. Battery 1130 as power supply is positioned in recess 1111 of the body, and LEDs 1135 are embedded in the watchband. Battery 1130 is connected to LEDs 1135 with wires shown as curved dotted lines 1137a-b for simplicity. The wires are connected to conductive locking pin 1140 that holds the watchband in place when assembled with the body. The locking pin can be constructed in three segments with two conductive ends and a non conductive middle. The locking pin can also comprise two separate pins inserted from each side such that the pins do not touch in the middle being separated by air or nonconductive material. The pin(s) provide the electrical connection from battery 1130 to LEDs 1135 such that the LEDs illuminate watchband 1120 as indicated by arrows 1136.

Figure 11B:
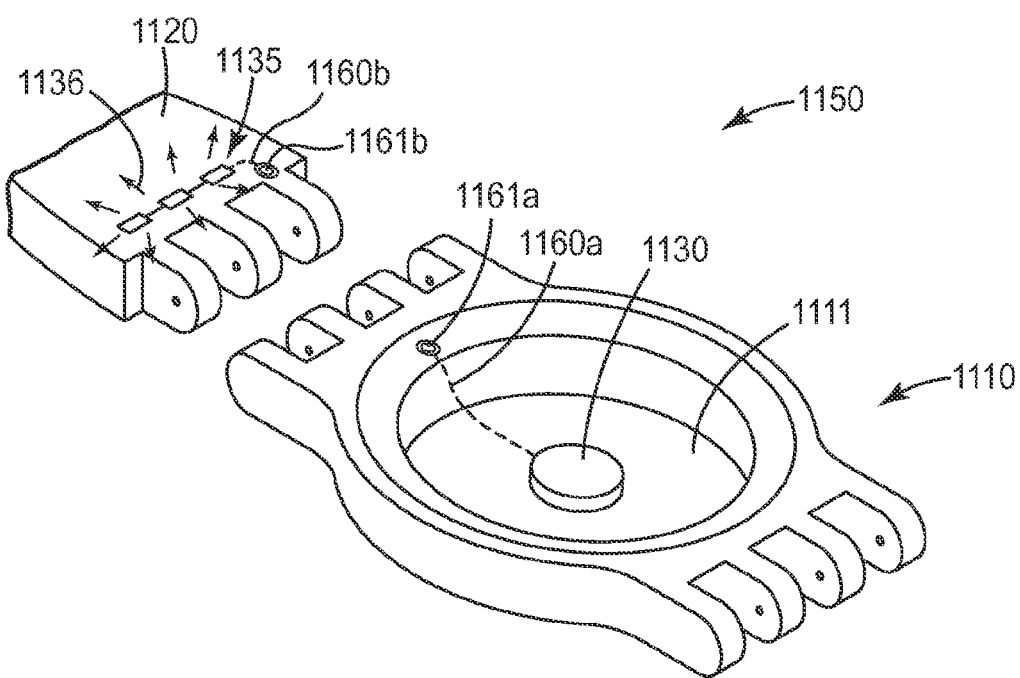

FIG. 11b shows an embodiment of watch 1150 in which battery 1100 supplies power to LEDs 1135 by induction. Wires shown generically as dotted line 1160a connect battery 1100 to induction coil 1161a, and wires shown generically as dotted line 1160b connect LEDs 1135 to induction coil 1161b. Alternatively, induction coils 1161a and 1161b could be replaced with RF transmitting and receiving antennas, respectively, such that the LEDs are powered remotely be RF signals. The closeness of the watch body and band is certain and the Send would be in the watch body, while the pick up/receiver could be located in the watch band where it could power the needed light source.

For the embodiments shown in FIGS. 11a-b, the battery and LEDs can be located in any combination of body and watchband. For example, the battery could be located in one or both watchbands, and/or the LEDs can be located in the body to light the watch face.

A watch body could be used with different watchbands as desired by the wearer.

Example 2

Illuminated Labels

A coil antenna tuned to the a 3M™ badging device was wired to 3 LEDs in series. Upon placing the antenna close (1 inch or less) to the badge reader, the LEDS would power on and could be observed to light up brightly.

A device was assembled as by placing three LEDS in both optical and physical contact with an edge of a layer of a viscoelastic lightguide (VEL). The LEDs were wired in series and connected to a coil antenna tuned to a 3M™ badging device. A graphic was adhered to one surface of the VEL and the opposing surface of the VEL was adhered to a plastic bottle. The VEL held the graphic to the bottle and the LEDs were also held in the VEL. Upon bringing this bottle with this "VEL Label" close to the badging device (within an inch), the LEDs powered on and light was seen illuminating the graphic on the bottle.

Example 3

Illuminated Labels

Figure 12:
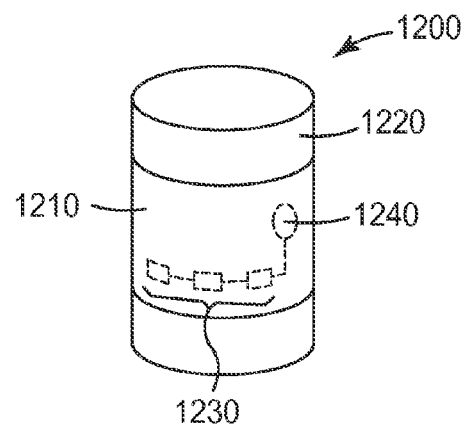
FIG. 12 is a schematic illustration of a smart-labeled can comprising an exemplary illumination device.

FIG. 12 shows smart-labeled can 1200 comprising label 1210 adhered to can 1220. Embedded within the label (or behind the label) are three LEDs 1230 wired in series and in communication with RF receiving antenna 1240.

Figure 13A:
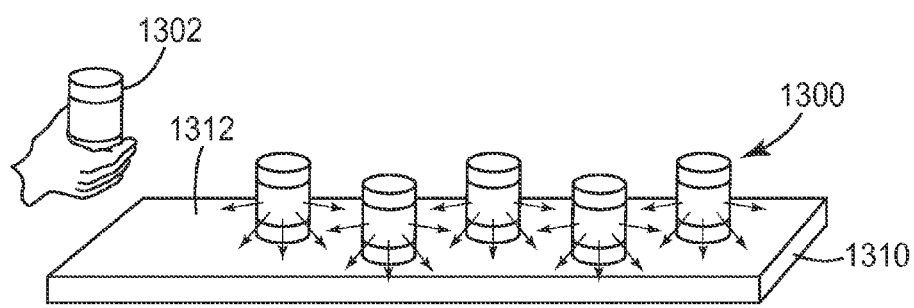
FIGS. 13a-c are schematic illustrations of a "smart inventory" system in which an exemplary illumination device is used.
Figure 13B:
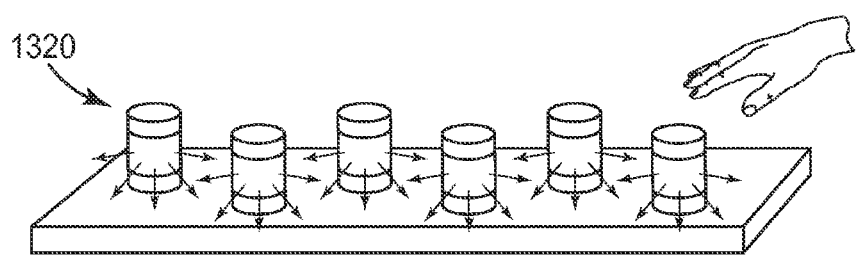
Figure 13C:
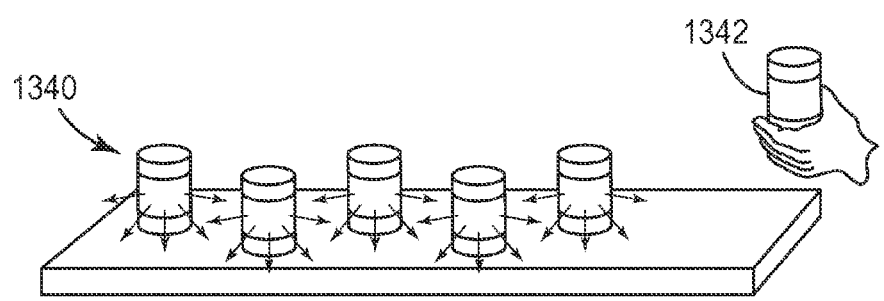

FIGS. 13a-c show schematic illustrations of a "smart inventory" system in which smart-labeled cans 1300 emit light when displayed on smart shelf 1310 having a power transmitter (not shown) across top surface 1312 of the shelf The cans are tracked by RFID from an inventory warehouse to the store and shelf where they are displayed. Light is not being emitted by smart-labeled can 1302 until it is placed on smart shelf 1310 to form smart-labeled cans 1320. Light is not emitted by smart-labeled can 1342 after it has been taken off smart shelf 1310 leaving smart-labeled cans 1342.

The closeness of a labeled can and power transmitter is certain as most labeled products are displayed on a shelf for consumption and purchase. The Send would be located in or on the shelf (maybe in a separate powered mat or sheet) where the product with the receiving LED illuminated label is to be displayed, while the pick up/receiver could be located in the label where it could power the needed light source to illuminate the label on the product only when placed on the power mat that is on the shelf. This means that the LEDs in the label will only be lit when the product is on the display and not during shipping, storage in warehouse or other non visible or needed places in the supply chain cycle. Illustration is shown in the figure below. The remote power source may be located in a shelf, display case for jewelry and other items, coat rack, refrigerator, cooler for cans.

Example 4

Bandages and Wound Dressings

A bandage or wound dressing could be equipped with a lightguide, a light source and a transducer having an RFID induction powered antenna. Light emitted by the light source could be used for antimicrobial treatment.

What is claimed is:

1. A refrigeration illumination system, comprising
  a light source;
  a lightguide optically coupled to the light source; and
  a transducer configured to power the light source by converting energy received from a remote transmitter;
  wherein at least one of the lightguide and the remote transmitter is located within a shelf.

2. The refrigeration illumination system of claim 1, wherein the light source, the lightguide, and the transducer are located within a product label.

3. The refrigeration illumination system of claim 1, wherein the remote transmitter is located in the shelf.

4. The refrigeration illumination system of claim 1, wherein the lightguide is located within the shelf.

5. An illumination device, comprising:
  a light source;
  a film lightguide optically coupled to the light source; and
  a transducer configured to power the light source by converting energy received from a remote transmitter.

6. The illumination device of claim 5, wherein the film lightguide is a rectangular layer.

7. An illumination device, comprising:
  a light source;
  a lightguide optically coupled to the light source;
  a viscoelastic cladding layer disposed on the lightguide; and
  a transducer configured to power the light source by converting energy received from a remote transmitter.

8. The illumination device of claim 7, wherein the viscoelastic cladding layer includes a pressure sensitive adhesive.

* * * * *